(12) United States Patent
Kavuru

(10) Patent No.: US 11,524,953 B2
(45) Date of Patent: Dec. 13, 2022

(54) NIRAPARIB SOLID STATE FORM

(71) Applicant: JOHNSON MATTHEY PUBLIC LIMITED COMPANY, London (GB)

(72) Inventor: Padmini Kavuru, Townsend, MA (US)

(73) Assignee: Macfarlan Smith Limited, Edinburgh (GB)

( * ) Notice: Subject to any disclaimer, the term of this patent is extended or adjusted under 35 U.S.C. 154(b) by 0 days.

(21) Appl. No.: 17/301,465

(22) Filed: Apr. 5, 2021

(65) Prior Publication Data

US 2021/0221787 A1 Jul. 22, 2021

Related U.S. Application Data

(60) Provisional application No. 62/879,844, filed on Jul. 29, 2019, provisional application No. 62/741,813, filed on Oct. 5, 2018.

(51) Int. Cl.
 *C07D 401/02* (2006.01)
 *C07D 401/10* (2006.01)
 *C07C 309/30* (2006.01)

(52) U.S. Cl.
 CPC .......... *C07D 401/10* (2013.01); *C07C 309/30* (2013.01)

(58) Field of Classification Search
 CPC .................................................... C07D 401/02
 See application file for complete search history.

(56) References Cited

U.S. PATENT DOCUMENTS

| 8,071,623 | B2 | 12/2011 | Jones et al. |
| 8,436,185 | B2 * | 5/2013 | Foley ........................ A61P 9/00 546/199 |
| 2017/0137403 | A1 | 5/2017 | Chung et al. |

FOREIGN PATENT DOCUMENTS

| CN | 107663190 A | 2/2018 | |
| WO | 2018183354 A1 | 10/2018 | |
| WO | WO-2018183354 A1 * | 10/2018 | ........... A61K 31/454 |

\* cited by examiner

*Primary Examiner* — John S Kenyon

(57) ABSTRACT

The present disclosure relates to a stabilized anhydrous p-toluenesulfonic acid salt of niraparib, Form A. The present disclosure is also related to processes for the preparation of the stabilized anhydrous p-toluenesulfonic acid salt of niraparib. Further, the present disclosure also relates to pharmaceutical compositions comprising the stabilized anhydrous p-toluenesulfonic acid salt of niraparib and methods for treating disease using the stabilized anhydrous p-toluenesulfonic acid salt of niraparib.

16 Claims, 4 Drawing Sheets

NIRAPARIB SOLID STATE FORM

CROSS-REFERENCE TO RELATED APPLICATIONS

This application is a continuation of international application No. PCT/US2019/054627, filed Oct. 4, 2019, which claims priority to U.S. Provisional Patent Application Nos. 62/741,813, filed Oct. 5, 2018, and 62/879,844, filed Jul. 29, 2019, the disclosures of which are incorporated herein by reference in their entireties for all purposes.

FIELD OF THE DISCLOSURE

The present invention is directed to a solid-state form of a p-toluenesulfonic acid salt of niraparib; particularly a stabilized anhydrous form. Further, the present disclosure is also related to a process for the preparation of the stabilized anhydrous form of the p-toluenesulfonic acid salt of niraparib. Further, the present disclosure also relates to pharmaceutical compositions comprising the stabilized anhydrous form of the p-toluenesulfonic acid salt of niraparib, and methods for treating disease using the stabilized anhydrous form of the p-toluenesulfonic acid salt of niraparib.

BACKGROUND OF THE DISCLOSURE

Niraparib, having the chemical designation 2-[4-[(3S)-3-piperidyl]phenyl]-indazole-7-carboxamide, is a small molecule poly (ADP-ribose) polymerase (PARP) inhibitor. Niraparib is used to treat ovarian cancer. Niraparib has the following structure:

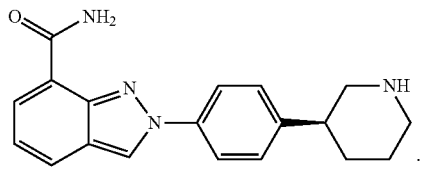 [SMILES: NC(=O)c1cccc2cn(-c3ccc([C@@H]4CCCNC4)cc3)nc12]

Niraparib is commercially marketed under the name Zejula. Niraparib is described in U.S. Pat. No. 8,071,623. A solid state form of niraparib, (3S)-3-{4-[7-(amino-carbonyl)-2H-indazol-2-yl]phenyl} piperidinium p-toluenesulfonate monohydrate, is disclosed in U.S. Pat. No. 8,436,185. WO2018183354 is directed to Form I, Form II and Form III of p-toluenesulfonic acid salt of niraparib, each substantially free of the other two forms. WO2018183354 discloses that Form I is a monohydrate of p-toluenesulfonic acid salt of niraparib, Form II is a non-stoichiometric hydrate of p-toluenesulfonic acid salt of niraparib prepared under anhydrous conditions, and Form III is an anhydrous form of the p-toluenesulfonic acid salt of niraparib. Furthermore, WO2018183354 discloses that "[i]n some embodiments, about: 80%, 85%, 90%, 95%, or 100% (e.g., about 95%) of the crystalline Form I of niraparib tosylate monohydrate is stable for 30 days or more." On the other hand, WO2018183354 does not disclose anything about the stability of Form II, but does state that "[t]he DVS curve of the anhydrate [(Form III)] is very hygroscopic and showed a weight gain of approximately 15.8% up to 95% RH . . . . The anhydrate converted to the monohydrate." In addition, WO2018183354 fails to disclose: 1) a preparation of anhydrous p-toluenesulfonic acid salt of niraparib under anhydrous conditions, and 2) a stabilized anhydrous form of p-toluenesulfonic acid salt of niraparib.

SUMMARY OF THE DISCLOSURE

The present invention is directed to a solid-state form of a p-toluenesulfonic acid salt of niraparib; particularly a stabilized anhydrous form, designated as Form A anhydrous p-toluenesulfonic acid salt of niraparib. Further, the present disclosure is also related to a process for the preparation of the stabilized anhydrous form of the p-toluenesulfonic acid salt of niraparib. Further, the present disclosure also relates to pharmaceutical compositions comprising the stabilized anhydrous form of the p-toluenesulfonic acid salt of niraparib, and methods for treating disease using the stabilized anhydrous form of the p-toluenesulfonic acid salt of niraparib.

DETAILED DESCRIPTION OF THE DISCLOSURE

Figure 1:
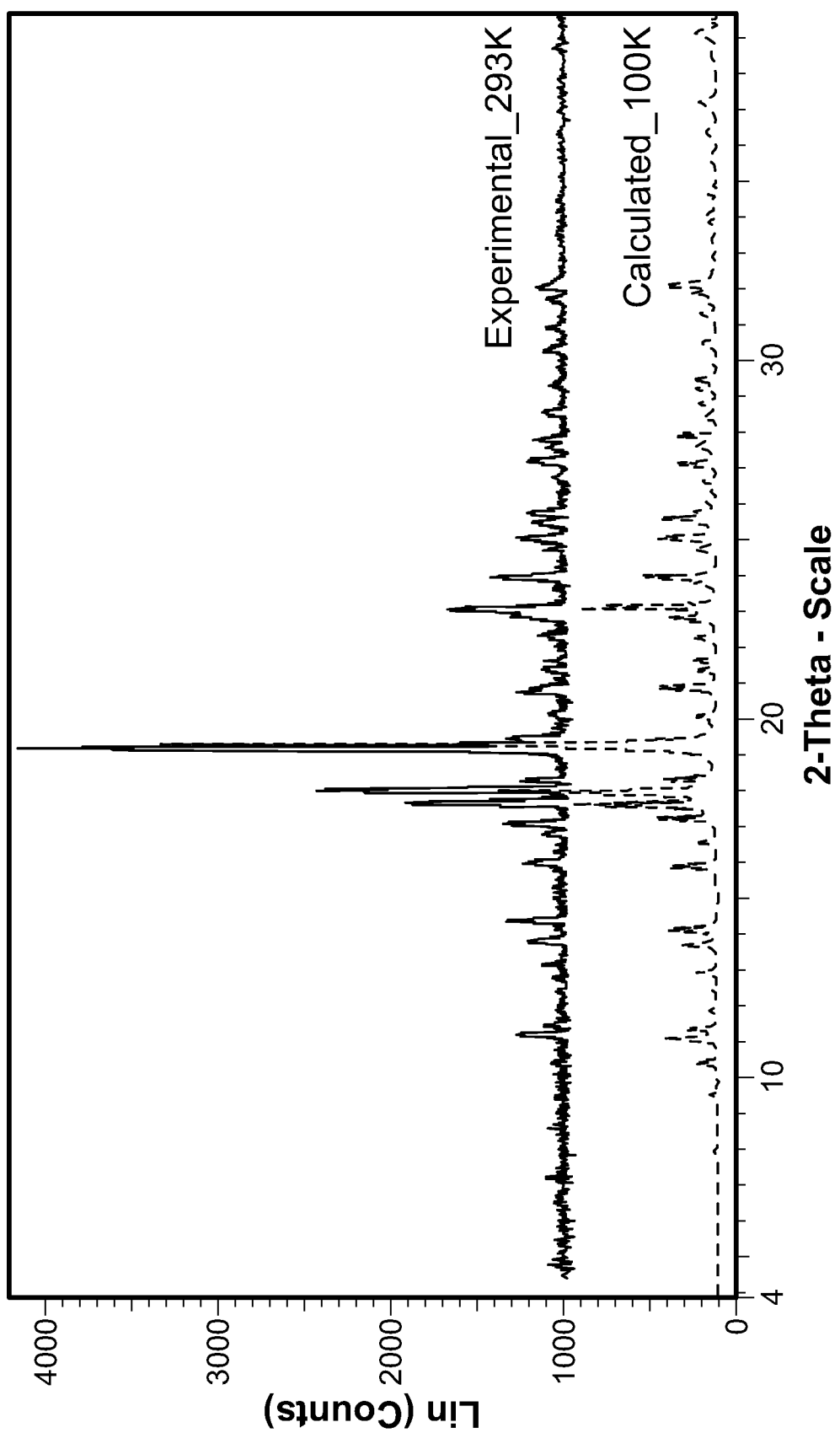
FIG. 1 represents the experimental and calculated XRPD patterns of Form A anhydrous p-toluenesulfonic acid salt of niraparib.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are not intended to be limited to the examples described herein and shown but are to be accorded the scope consistent with the claims.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by XRPD; indicate that the value or range of values may deviate to an extent deemed reasonable to one of ordinary skill in the art while still describing the particular solid form.

As used herein and unless otherwise specified, the term "pharmaceutical composition" is intended to encompass a pharmaceutically effective amount of Form A anhydrous p-toluenesulfonic acid salt of niraparib and a pharmaceutically acceptable excipient. As used herein, the term "pharmaceutical compositions" includes pharmaceutical compositions such as tablets, pills, powders, liquids, suspensions, emulsions, granules, capsules, suppositories, or injection preparations.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

As used herein and unless otherwise specified, the term "excipient" refers to a pharmaceutically acceptable organic or inorganic carrier substance. Excipients may be natural or synthetic substances formulated alongside the active ingredient of a medication, included for bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance, such as by facilitating powder flowability or non-stick properties, in addition to aiding in vitro stability such as prevention of denaturation over the expected shelf life.

As used herein and unless otherwise specified, the term "patient" refers to an animal, preferably a mammal, most preferably a human, who has been the object of treatment, observation or experiment. Preferably, the patient has experienced and/or exhibited at least one symptom of the disease or disorder to be treated and/or prevented. Further, a patient may not have exhibited any symptoms of the disorder, disease or condition to be treated and/or prevented, but has been deemed by a physician, clinician or other medical professional to be at risk for developing said disorder, disease or condition.

As used herein and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more therapeutic agents to a patient with such a disease or disorder. In some embodiments, the terms refer to the administration of a compound provided herein, with or without other additional active agents, after the onset of symptoms of a disease.

"Stabilized" as used herein relates to an anhydrous form of the p-toluenesulfonic acid salt of niraparib that is capable of retaining its form for up to at least 4 months when held in storage in a sealed container with desiccant, with or without being stored in a foiled bag.

Stabilized anhydrous p-toluenesulfonic acid salt of niraparib, Form A, is prepared under anhydrous conditions and the process comprises,
   a. adding a solution of anhydrous p-toluene sulfonic acid in an anhydrous polar organic solvent to an anhydrous solution of niraparib in an anhydrous polar organic solvent at an elevated temperature under a dry atmosphere;
   b. stirring the resultant mixture of solutions at a reduced temperature overnight to precipitate anhydrous p-toluenesulfonic acid salt of niraparib under a dry atmosphere;
   c. isolating the precipitated anhydrous p-toluenesulfonic acid salt of niraparib; and
   d. placing the precipitated anhydrous p-toluenesulfonic acid salt of niraparib in a sealed vial, with desiccant, and optionally with or without sealing the vial in a foil bag.

Furthermore, the present invention also relates to pharmaceutical compositions comprising stabilized Form A anhydrous p-toluenesulfonic acid salt of niraparib and a pharmaceutically acceptable carrier. Pharmaceutical compositions comprising the p-toluenesulfonic acid salt of niraparib may be prepared according to U.S. Pat. No. 8,436,185, which is incorporated herein by reference in its entirety. The dosage of the pharmaceutical compositions may be varied over a wide range. Optimal dosages and dosage regimens to be administered may be readily determined by those skilled in the art, and will vary with the mode of administration, the strength of the preparation and the advancement of the disease condition. In addition, factors associated with the patient being treated, including patient's sex, age, weight, diet, physical activity, time of administration and concomitant diseases, will result in the need to adjust dosages and/or regimens. For example, a dosage of the pharmaceutical composition of the invention is available as 3×100 mg tablets. The recommended dose of niraparib is 300 mg (461.3 mg of anhydrous p-toluenesulfonic acid salt of niraparib) once daily and may be used as monotherapy or in combination with methotrexate or other DMARDs.

Furthermore, the present invention also relates to a method for treating a disease using stabilized Form A anhydrous p-toluenesulfonic acid salt of niraparib; more particularly treating recurrent epithelial ovarian, fallopian tube, or primary peritoneal cancer.

EXAMPLES

Examples, which follow herein, are directed to embodiments of the invention. The examples are presented to enable a person of ordinary skill in the art to make and use the various embodiments. Descriptions of specific devices, techniques, and applications are provided only as examples. Various modifications to the examples described herein will be clear to those of ordinary skill in the art, and the general principles described herein may be applied to other examples and applications without departing from the spirit and scope of the various embodiments. Therefore, the various embodiments are illustrative of the present disclosure and the disclosure is not intended to be limited to the examples described herein and shown.

Analytical Techniques

XRPD patterns are obtained using a Bruker D8 Advance equipped with a Cu Kα radiation source ($\lambda=1.54$ Å), a 9-position sample holder and a LYNXEYE super speed detector. Samples are placed on air sensitive silicon plate holders with zero-background with domes for analysis. One skilled in the art would recognize that the ° 2θ values and the relative intensity values are generated by performing a peak search on the measured data and the d-spacing values are calculated by the instrument from the ° 2θ values using Bragg's equation. One skilled in the art would further recognize that the relative intensity for the measured peaks may vary because of sample preparation, orientation and instrument used, for example.

DSC data are collected using a TA Instruments Q10 DSC. Approximately, samples (2-8 mg) are placed in unsealed but covered hermetic alodined aluminum sample pans and scanned from about 30° C. to about 300° C. at a rate of about 10° C./min under a nitrogen purge of about 50 mL/min. Some of the DSC runs are generated on a TA Instruments Q2000 equipped with an auto-sampler and RSC40 cooling unit. The sampling is conducted at a ramp rate of about 10° C./min from 20° C. to 320° C. using To hermetic sealed aluminum sample pans in T4P (or T3) mode.

TGA measurements are recorded using a TA Q500 instrument. Approximately, 2-5 mg samples are placed in a pin holed sealed hermetic alodined aluminum DSC pan, pre-tared with an aluminum pan. TGA investigations are performed at a heating rate of about 10° C./min over a temperature range of from about 30° C. to about 300° C., with purging with nitrogen at a flow rate of about 60 mL/min.

$^1$H-NMR data is collected using a Bruker Avance 300 MHz NMR equipped with TopSpin software. Samples are prepared by dissolving the compound in deuterated dimethylsulfoxide with 0.05% (v/v) tetramethylsilane (TMS). The number of scans is 16 for $^1$H-NMR.

EXPERIMENTAL

Examples below provide embodiments of the preparation of anhydrous p-toluenesulfonic acid salt of niraparib, Form A.

Example 1

Form A anhydrous p-toluenesulfonic acid salt of niraparib is prepared by dissolving 200 mg of p-toluenesulfonic acid salt of niraparib in 0.5 mL of a solvent selected from N-methyl-2-pyrrolidone (NMP) or dimethylsulfoxide (DMSO) at 60° C., followed by the addition of a volume (mL) of anti-solvent selected from the group consisting of acetone (ACE), isopropanol (IPA), isopropyl acetate (IPAc), ethyl formate (EF), acetonitrile (MeCN), methyl ethyl ketone (MEK), tetrahydrofuran (THF), 2-methyltetrahydrofuran (Me-THF), cyclopentyl methyl ether (CPME) and ethyl acetate (EtOAc), as shown in Table I. Resultant precipitant is then analyzed by XRPD.

TABLE 1

Summary of anti-solvent addition experiments

| Dissolving solvent, mL | Anti-solvent, mL | XRPD result |
| --- | --- | --- |
| NMP. 0.5 | ACE, 1.5 | Form A |
| NMP. 0.5 | THF, 2 | Form A |
| NMP. 0.5 | IPA, 1.5 | Form A |
| NMP. 0.5 | IPAc, 1.5 | Form A |
| NMP. 0.5 | EF, 1.5 | Form A |
| NMP. 0.5 | MeCN, 1.5 | Form A |
| NMP. 0.5 | MEK, 1.5 | Form A |
| NMP. 0.5 | Me-THF, 1.5 | Form A |
| NMP. 0.5 | CPME, 1 | Form A |
| NMP. 0.5 | EtOAc, 1 | Form A |
| DMSO, 0.5 | ACE, 1.5 | Form A |
| DMSO, 0.5 | MeCN, 1.5 | Form A |
| DMSO, 0.5 | MEK, 1.5 | Form A |
| DMSO, 0.5 | CPME, 1.5 | Form A |
| DMSO, 0.5 | IPA, 1.5 | Form A |
| DMSO, 0.5 | IPAc, 1.5 | Form A |
| DMSO, 0.5 | EF, 1.5 | Form A |
| DMSO, 0.5 | EtOAc, 1.5 | Form A |
| DMSO, 0.5 | Me-THF, 1.5 | Form A |

Example 2

Form A anhydrous p-toluenesulfonic acid salt of niraparib is prepared by dissolving 200 mg of p-toluenesulfonic acid salt of niraparib in 0.5 mL of dimethyl formamide (DMF) at 60° C., followed by the addition of 2 mL, in 0.5 mL increments, of anti-solvent selected from the group consisting of isopropanol (IPA), 1-propanol (1-PrOH), isopropyl acetate (IPAc), ethyl formate (EF), acetonitrile (MeCN), t-butyl methyl ether (TBME), tetrahydrofuran (THF), 2-methyltetrahydrofuran (Me-THF), cyclopentyl methyl ether (CPME), ethanol (EtOH) and ethyl acetate (EtOAc), as shown in Table II. Resultant precipitant is then analyzed by XRPD.

TABLE II

Summary of step-wise addition of anti-solvent addition experiments

| Dissolving solvent, mL | Anti-solvent, mL | XRPD |
| --- | --- | --- |
| DMF, 0.5 | CPME, 2 | Form A |
| DMF, 0.5 | EF, 2 | Form A |
| DMF, 0.5 | IPA, 2 | Form A |
| DMF, 0.5 | EtOH, 2 | Form A |
| DMF, 0.5 | THF, 2 | Form A |
| DMF, 0.5 | MeCN, 2 | Form A |
| DMF, 0.5 | TBME, 2 | Form A |
| DMF, 0.5 | IPAc, 2 | Form A |
| DMF, 0.5 | Me-THF, 2 | Form A |
| DMF, 0.5 | EtOAc, 2 | Form A |
| DMF, 0.5 | 1-PrOH, 2 | Form A |

Example 3

Form A anhydrous p-toluenesulfonic acid salt of niraparib is prepared by dissolving 200 mg of p-toluenesulfonic acid salt of niraparib in 1 mL of a solvent selected from the group consisting of DMF, NMP and DMSO at 50° C. The formed solution is then added dropwise to 2 mL of an anti-solvent selected from the group consisting of acetone (ACE), acetonitrile (MeCN), tetrahydrofuran (THF), cyclopentyl methyl ether (CPME), and ethyl acetate (EtOAc), as shown in Table III. Resultant precipitant is then analyzed by XRPD.

TABLE III

Summary of reverse anti-solvent addition experiments

| Anti-solvent, 2 mL | Dissolving solvent, mL | XRPD result |
| --- | --- | --- |
| EtOAc | DMF, 1 | Form A |
| THF | DMF, 1 | Form A |
| CPME | DMF, 1 | Form A |
| MeCN | NMP, 1 | Form A |
| Acetone | NMP, 1 | Form A |
| THF | DMSO, 1 | Form A |
| EtAOc | DMSO, 1 | Form A |
| Acetone | DMSO, 1 | Form A |

Example 4

Preparation of Form A Anhydrous P-Toluenesulfonic Acid Salt of Niraparib Under Anhydrous Conditions 5 g of niraparib free base is dissolved in 20 mL of anhydrous DMSO at 70° C. 18.02 g (1.1 equivalent) of anhydrous p-toluene sulfonic acid (p-TSA; prepared by azeotroping of water from reagent grade of p-TSA using IPAc) in 15 mL IPAc (dried over molecular sieves) and 15 mL of IPA (anhydrous) is added slowly (rate of addition-1 mL/min) to the niraparib solution. The temperature of the mixed solutions is reduced to 5° C., and the mixed solution is stirred overnight (18-20 h). The reaction is carried out in a 100 mL EasyMax reactor under nitrogen flow. After the stirring period, precipitant is observed, filtered and rinsed with an additional 10-15 mL of IPAc (dried over molecular sieves). The isolated precipitant is dried in the oven under vacuum at 60° C. for 24 h. Yield 85%. Formation of Form A anhydrous p-toluenesulfonic acid salt of niraparib is confirmed by XRPD, NMR, DSC/TGA.

FIG. 1 represents the experimental and calculated XRPD patterns of Form A anhydrous p-toluenesulfonic acid salt of niraparib obtained by the instant method. Form A anhydrous p-toluenesulfonic acid salt of niraparib is characterized by its XRPD pattern peaks as listed in Table IV below.

TABLE IV

| Angle 2Θ° | Intensity % % |
|---|---|
| 11.1 | 9.5 |
| 14.2 | 11.8 |
| 15.9 | 10.8 |
| 17.2 | 10.9 |
| 17.6 | 26 |
| 17.9 | 43.1 |
| 18.3 | 9.5 |
| 19.3 | 100 |
| 20.9 | 10.5 |
| 23.1 | 24.8 |
| 24.0 | 13 |
| 25.0 | 11.1 |
| 25.6 | 10.3 |
| 27.1 | 8.4 |
| 27.9 | 9.1 |
| 32.1 | 9.3 |

The angle measurements are ±0.2° 2 Θ. Key defining peaks for solid-state Form A anhydrous p-toluenesulfonic acid salt of niraparib include one or more of 17.9, 17.6, 19.3, and 23.1° 2 Θ degrees.

Figure 2:
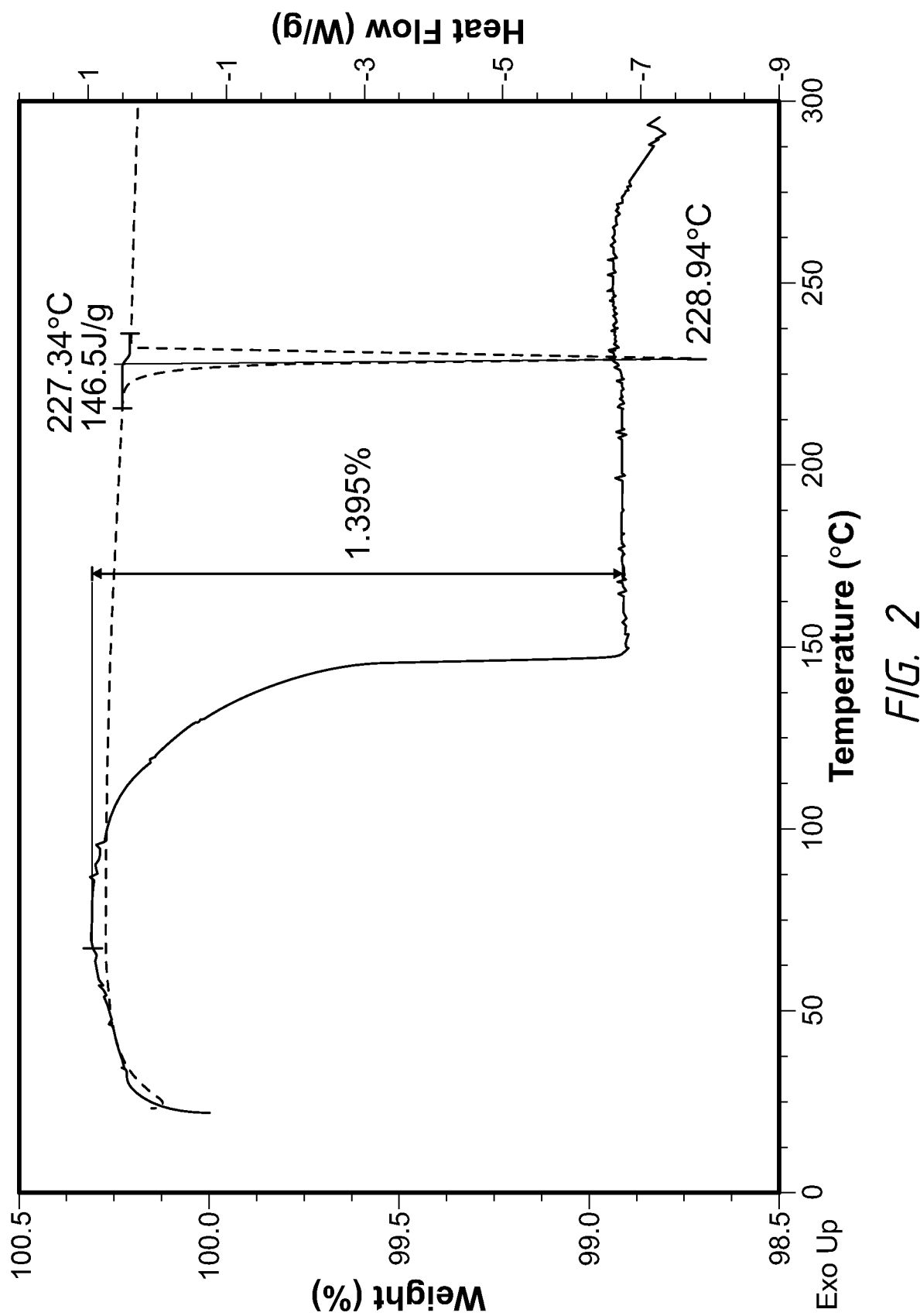
FIG. 2 shows TGA and DSC plots of Form A anhydrous p-toluenesulfonic acid salt of niraparib.
Figure 3:
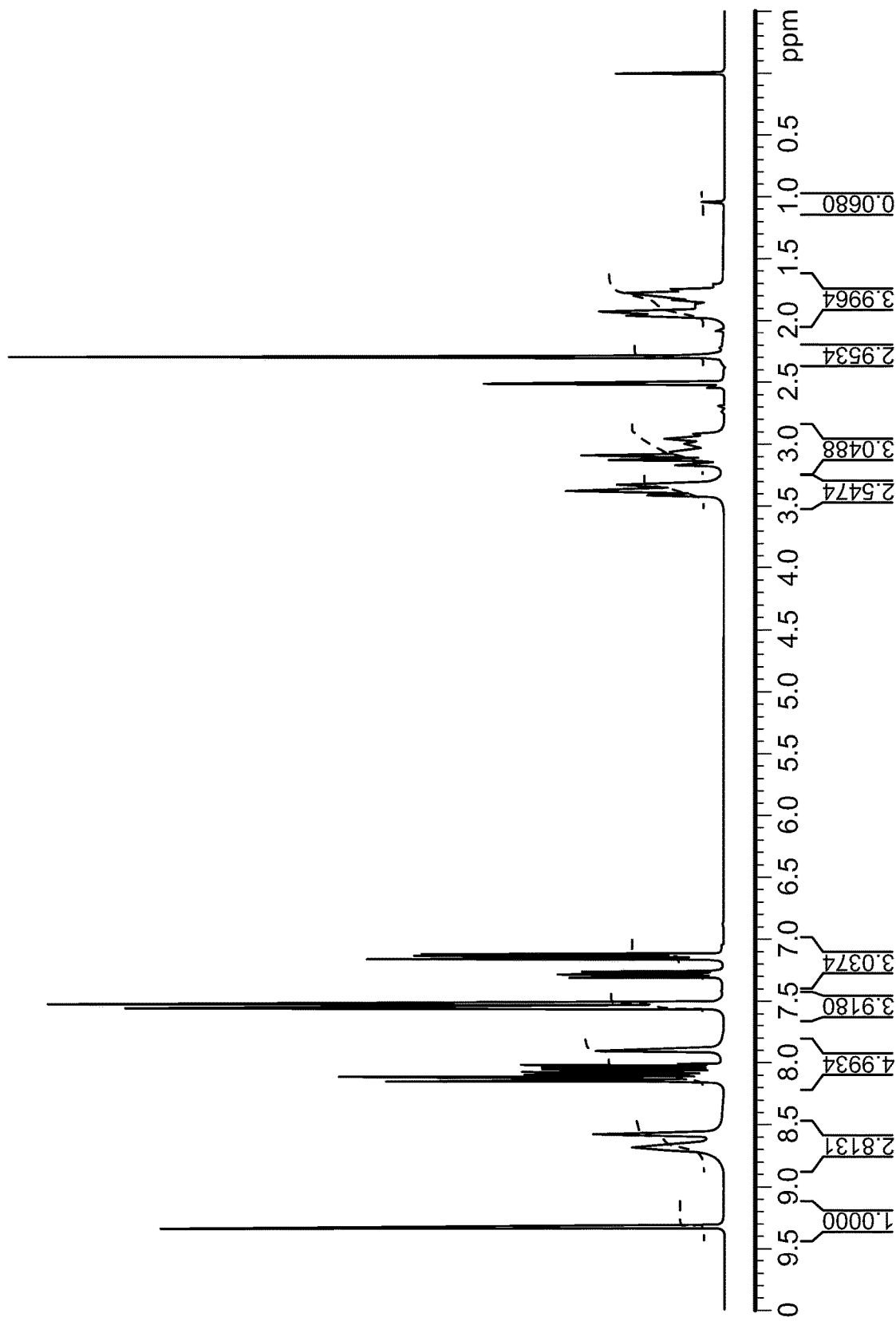
FIG. 3 is a $^1$H NMR spectra of Form A anhydrous p-toluenesulfonic acid salt of niraparib.

FIG. 2 represents a TGA plot that shows a weight loss of about 1.4% from about 100° C. through about 145° C. (expected to be residual solvent), and DSC plot shows onset of a thermal event at 227° C. and the thermal event at about 229° C. for Form A anhydrous p-toluenesulfonic acid salt of niraparib. FIG. 3 is an $^1$H NMR spectra for Form A anhydrous p-toluenesulfonic acid salt of niraparib.

Single crystals of Form A anhydrous p-toluenesulfonic acid salt of niraparib are obtained by drying Form A anhydrous p-toluenesulfonic acid salt of niraparib (about 100 mg dissolved in about 1 mL DMF) at about 45° C. under vacuum for about 48 h. SCXRD data is solved at about 100 K.

The single crystal parameters for Form A anhydrous p-toluenesulfonic acid salt of niraparib as determined by SCXRD are:
Space Group: Triclinic, P1
a=9.8 Å±1.5%
b=11.2 Å±1.5%
c=11.7 Å±1.5%
α=87±3°, β=72°±+3°, γ=84°±3°
Volume: 1216 Å$^3$±3%
Z=2, Z'=2

Figure 4:
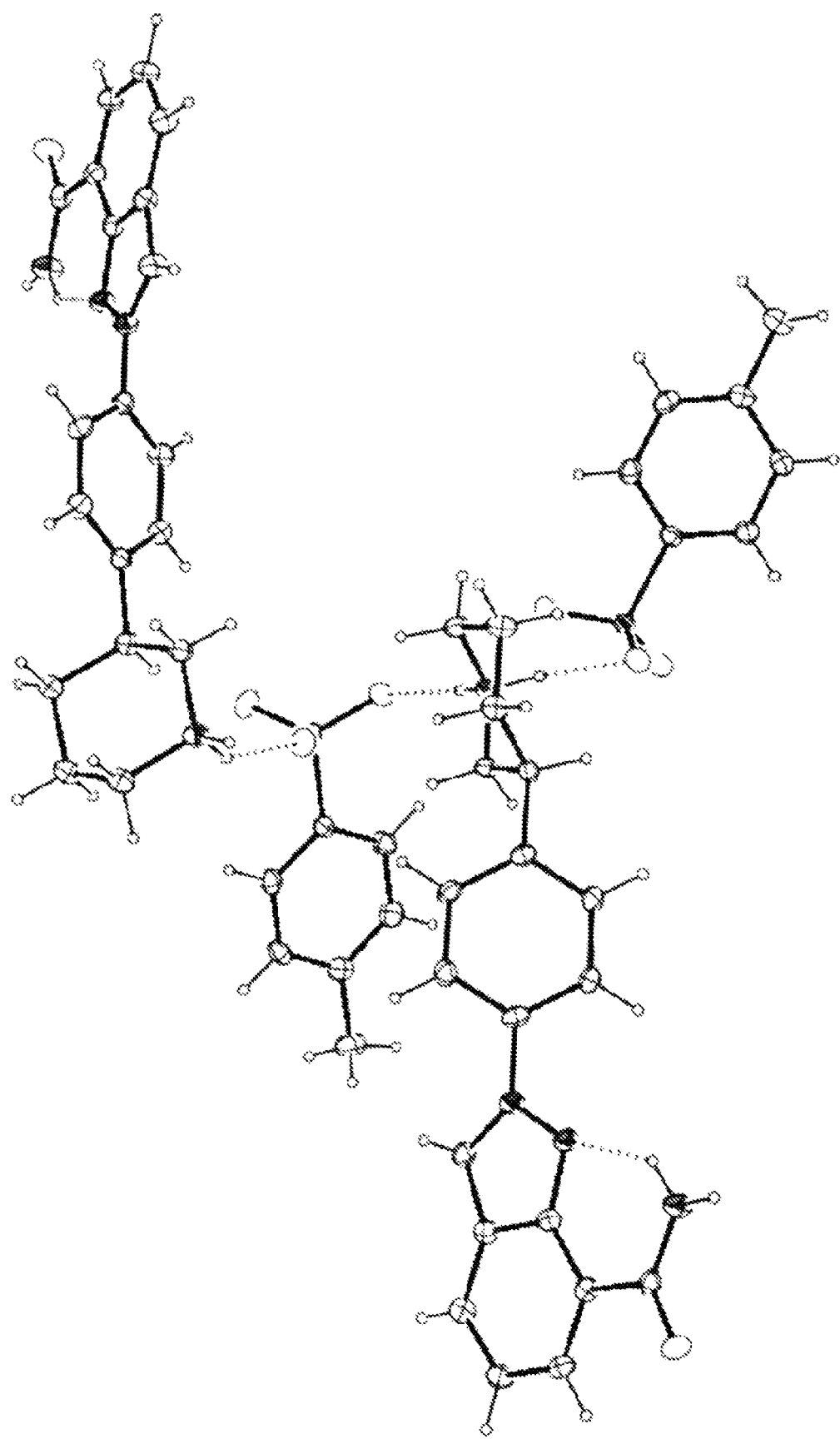
FIG. 4 represents the asymmetric unit of Form A anhydrous p-toluenesulfonic acid salt of niraparib.

FIG. 4 shows the asymmetric unit of Form A anhydrous p-toluenesulfonic acid salt of niraparib.

The SCRXD analysis of Form A anhydrous p-toluenesulfonic acid salt of niraparib reveals the presence of two niraparib molecules along with two tosylate molecules in the asymmetric unit. The crystal structure of Form A anhydrous p-toluenesulfonic acid salt of niraparib reveals that the one of the niraparib molecules forms an intermolecular hydrogen-bond with another niraparib molecule through the amide dimer and the tosylate interacts with the amino group on the six-membered ring.

Example 5

Preparation of Form A Anhydrous P-Toluenesulfonic Acid Salt of Niraparib Under Anhydrous Conditions 7.2 g of niraparib free base is dissolved in 36 mL of anhydrous DMSO at 70° C. 22.5 g (1.1 equivalent) of anhydrous p-toluene sulfonic acid (p-TSA; prepared by azeotropic distillation of water from reagent grade of p-TSA by rotovap with EtOAc (3 chases) and the final chase by IPA to decrease the % water from about 1.14% to about 0.031%) in 24 mL IPAc (dried over molecular sieves) and 24 mL of IPA (anhydrous) is added slowly (rate of addition-2 mL/min) to the niraparib solution. The temperature of the mixed solutions is reduced to 5° C. at the rate of 2° C./min, and the mixed solution is stirred overnight (18-20 h). The reaction is carried out in a 100 mL EasyMax reactor under nitrogen flow. After the stirring period, precipitant is observed, filtered and rinsed with an additional 10-15 mL of IPAc (dried over molecular sieves). The isolated precipitant is dried in the oven under vacuum at 60° C. for 24 h.

Example 6

Anhydrous p-toluenesulfonic acid salt of niraparib, Form A, not made under anhydrous conditions (Examples 1-3) does not exhibit extended stability comparable to Form A anhydrous p-toluenesulfonic acid salt of niraparib made under anhydrous conditions such as described in Example 4 or 5. Furthermore, the anhydrous p-toluenesulfonic acid salt of niraparib, Form A, made under anhydrous conditions exhibits extended stability of at least 4 months, as evidenced by XRPD analyses of samples of Form A, when stored in sealed vials, with desiccant, with and without sealing in a foil bag, at ambient conditions, 30° C./65% RH or 40° C./75% RH, whereas samples of Form A stored only in sealed vials, i.e., without desiccant, with and without sealing in a foil bag, do not exhibit the extended stability.

The above examples are presented to aid in the understanding of the disclosure and to enable a person of ordinary skill in the art to make and use the various embodiments and are not intended and should not be construed to limit in any way the disclosure set forth in the claims which follow hereafter.

What is claimed is:

1. Stabilized anhydrous p-toluenesulfonic acid salt of niraparib prepared under anhydrous conditions.

2. The stabilized anhydrous p-toluenesulfonic acid salt of niraparib of claim 1 wherein the preparation under anhydrous conditions comprises:
   a. adding a solution of anhydrous p-toluene sulfonic acid in an anhydrous polar organic solvent to an anhydrous solution of niraparib in an anhydrous polar organic solvent at an elevated temperature under a dry atmosphere;
   b. stirring the resultant mixture of solutions at a reduced temperature overnight to precipitate anhydrous p-toluenesulfonic acid salt of niraparib under a dry atmosphere;
   c. isolating the precipitated anhydrous p-toluenesulfonic acid salt of niraparib; and d. placing the precipitated anhydrous p-toluenesulfonic acid salt of niraparib in a sealed vial, with desiccant, and optionally with or without sealing the vial in a foil bag.

3. The stabilized anhydrous p-toluenesulfonic acid salt of niraparib of claim 2 wherein for the anhydrous solution of niraparib in an anhydrous polar organic solvent the anhydrous polar organic solvent is selected from DMSO, DMF, NMP, and mixtures thereof.

4. The stabilized anhydrous p-toluenesulfonic acid salt of niraparib of claim 2 wherein for the anhydrous solution of p-toluene sulfonic acid in an anhydrous polar organic solvent the polar organic solvent is selected from IPAC, IPA, ACE, MeCN, THF, CPME, EtOAc, and mixtures thereof.

5. The stabilized anhydrous p-toluenesulfonic acid salt of niraparib of claim 2 wherein for the anhydrous solution of p-toluene sulfonic acid in an anhydrous polar organic solvent the p-toluene sulfonic acid is prepared by azeotropic distillation to remove water.

6. The stabilized anhydrous p-toluenesulfonic acid salt of niraparib of claim 2 wherein the elevated temperature is at about 70° C.

7. The stabilized anhydrous p-toluenesulfonic acid salt of niraparib of claim 2 wherein the reduced temperature is at about 5° C.

8. The stabilized anhydrous p-toluenesulfonic acid salt of niraparib of claim 2 wherein the dry atmosphere is under nitrogen.

9. The stabilized anhydrous p-toluenesulfonic acid salt of niraparib of claim 1 that is Form A.

10. The stabilized anhydrous p-toluenesulfonic acid salt of niraparib of claim 9 wherein an onset of a thermal event is at about 227° C., as measured by differential scanning calorimetry.

11. The stabilized anhydrous p-toluenesulfonic acid salt of niraparib of claim 10 wherein the thermal event is at about 229° C., as measured by differential scanning calorimetry.

12. The stabilized anhydrous p-toluenesulfonic acid salt of niraparib of claim 9 which has single crystal parameters
a=9.8 Å±1.5%
b=11.2 Å±1.5%
c=11.7 Å±1.5%
α=87±3°, β=72°±+3°, γ=84°±3°.

13. The stabilized anhydrous p-toluenesulfonic acid salt of niraparib of claim 9 which has a cell volume of about 1216 Å$^3$±3%.

14. The stabilized anhydrous p-toluenesulfonic acid salt of niraparib of claim 9, characterized by having at least 2 or more X-ray powder diffraction peaks selected from about 17.9, 17.6, 19.3, and 23.1° 2Θ degrees±0.2° 2Θ.

15. A pharmaceutical composition comprising a pharmaceutically effective amount of the stabilized anhydrous p-toluenesulfonic acid salt of niraparib of claim 1 and a pharmaceutically acceptable excipient.

16. A process for the preparation of the stabilized anhydrous p-toluenesulfonic acid salt of niraparib according to claim 1 comprising,
   a. adding a solution of anhydrous p-toluene sulfonic acid in an anhydrous polar organic solvent to an anhydrous solution of niraparib in an anhydrous polar organic solvent at an elevated temperature under a dry atmosphere;
   b. stirring the resultant mixture of solutions at a reduced temperature overnight to precipitate anhydrous p-toluenesulfonic acid salt of niraparib under a dry atmosphere;
   c. isolating the precipitated anhydrous p-toluenesulfonic acid salt of niraparib; and
   d. placing the precipitated anhydrous p-toluenesulfonic acid salt of niraparib in a sealed vial, with desiccant, and optionally with or without sealing the vial in a foil bag.

* * * * *